US011806213B2

(12) United States Patent
Ono et al.

(10) Patent No.: US 11,806,213 B2
(45) Date of Patent: Nov. 7, 2023

(54) VOICE TRANSMISSION COMPENSATION APPARATUS, VOICE TRANSMISSION COMPENSATION METHOD AND PROGRAM

(71) Applicant: NIPPON TELEGRAPH AND TELEPHONE CORPORATION, Tokyo (JP)

(72) Inventors: Asuka Ono, Tokyo (JP); Momoko Nakatani, Tokyo (JP); Ai Nakane, Tokyo (JP); Yoko Ishii, Tokyo (JP)

(73) Assignee: NIPPON TELEGRAPH AND TELEPHONE CORPORATION, Tokyo (JP)

( * ) Notice: Subject to any disclaimer, the term of this patent is extended or adjusted under 35 U.S.C. 154(b) by 37 days.

(21) Appl. No.: 17/921,243

(22) PCT Filed: Apr. 30, 2020

(86) PCT No.: PCT/JP2020/018306
§ 371 (c)(1),
(2) Date: Oct. 25, 2022

(87) PCT Pub. No.: WO2021/220480
PCT Pub. Date: Nov. 4, 2021

(65) Prior Publication Data
US 2023/0157894 A1 May 25, 2023

(51) Int. Cl.
*A61F 11/04* (2006.01)
*G10L 21/16* (2013.01)
*G10L 21/18* (2013.01)
*G10L 25/87* (2013.01)
*G10L 25/51* (2013.01)
*G10L 25/78* (2013.01)

(52) U.S. Cl.
CPC .............. *A61F 11/045* (2013.01); *G10L 21/16* (2013.01); *G10L 21/18* (2013.01); *G10L 25/51* (2013.01); *G10L 25/87* (2013.01); *G10L 2025/783* (2013.01)

(58) Field of Classification Search
CPC ........ A61F 11/045; G10L 21/16; G10L 21/18; G10L 25/51; G10L 25/87; G10L 2025/783
See application file for complete search history.

(56) References Cited

U.S. PATENT DOCUMENTS

2005/0222845 A1* 10/2005 Nakagawa et al. G10L 21/0364
704/E21.009
2023/0005473 A1* 1/2023 Nakahara et al. .. G10L 15/1815

FOREIGN PATENT DOCUMENTS

JP   H11352876 A   12/1999
JP   2005287600 A   10/2005

OTHER PUBLICATIONS

Gick et al. (2009) "Aero-tactile integration in speech perception" Nature, 462(7272), 502.
(Continued)

*Primary Examiner* — Paras D Shah
*Assistant Examiner* — Athar N Pasha

(57) ABSTRACT

A speech transmission compensation apparatus that assists discrimination of speech heard by a user, includes: one or more computers each including a memory and a processor configured to: accept input of a speech signal, detect a specific type of sound in the speech signal, analyze an acoustic characteristic of the specific type of sound in the speech signal and output the acoustic characteristic; accept input of the acoustic characteristic being output by the memory and the processor, generate a vibration signal of a duration corresponding to the acoustic characteristic and output the vibration signal; and accept input of the vibration signal being output by the memory and the processor and provide the user with vibration for the duration on the basis of the vibration signal.

4 Claims, 8 Drawing Sheets

(56) References Cited

OTHER PUBLICATIONS

Masahiro Yoshikawa (1988) "Speech Perception through Vibrotactile Sensations by Hearing-Impaired People and the Role of a Single Vibrator", The Japanese Journal of Communication Disorders, No. 5, pp. 22-28.

\* cited by examiner

VOICE TRANSMISSION COMPENSATION APPARATUS, VOICE TRANSMISSION COMPENSATION METHOD AND PROGRAM

CROSS-REFERENCE TO RELATED APPLICATIONS

This application is a U.S. National Stage Application filed under 35 U.S.C. §371 claiming priority to International Patent Application No. PCT/JP2020/018306, filed on 30 Apr. 2020, the disclosure of which is hereby incorporated herein by reference in its entirety.

TECHNICAL FIELD

The present invention relates to a technology of assisting discrimination of speech being heard, through compensation of transmission of the speech to a user.

BACKGROUND ART

In a noisy environment or with hearing disorder, high-pitch sound and low-energy sound are less likely to be input to the human auditory sense. This particularly makes discrimination of consonants difficult, resulting in inhibition of clear hearing of whole speech and understanding of contents of the speech.

Non-Patent Literature 1 discloses a tactual vocoder as a conventional art of compensating transmission of speech. The tactual vocoder disclosed in Non-Patent Literature 1 divides a speech input into a plurality of bands and vibrates contact vibrators assigned to respective bands, to thereby tactually transmit spoken language to a person with hearing disorder.

In addition, Non-Patent Literature 2 discloses a phenomenon of generating an illusion and changing a way of being heard, as a result of artificially providing a tactual stimulus relating to an articulatory movement together with acoustic input of speech.

CITATION LIST

Non-Patent Literature

Non-Patent Literature 1: Masahiro Yoshikawa. (1988) Speech Perception through Vibrotactile Sensations by Hearing-Impaired People and the Role of a Single Vibrator (Shokushindokaku ni yoru choukaku shougai-ji no onsei chikaku to shindouki no yakuwari), The Japanese journal of communication disorders (Chono Gengogaku Kenkyu), 5, 22-28.

Non-Patent Literature 2: Gick, B., & Derrick, D. (2009), Aero-tactile integration in speech perception. Nature, 462(7272), 502.

SUMMARY OF THE INVENTION

Technical Problem

The tactual vocoder disclosed in Non-Patent Literature 1 has required training of a person with hearing disorder as a user, such as learning correspondence between vibration and speech, in order to use it. Consequently, the apparatus alone has not yet served in hearing assistance.

Leveraging the phenomenon disclosed in Non-Patent Literature 2 that a tactual stimulus relating to an articulatory movement is integrated with acoustic input of speech, can lead to more effective hearing assistance without requiring training. However, the tactual stimulus in the aforementioned phenomenon confirmed to be effective was limited to those requiring an elaborate apparatus such as a cylinder for generating an air jet and a haptic presentation apparatus for stretching skin, and was therefore not suitable for practical applications.

The present invention has been made in view of the above-described circumstances, and an object of the present invention is to provide a technology enabling realization of speech hearing assistance through leveraging tactual information in speech hearing, requiring neither training of a user nor an elaborate apparatus.

Means for Solving the Problem

The technology disclosed herein provides a speech transmission compensation apparatus that assists discrimination of speech heard by a user, including:
   an analysis unit that accepts input of a speech signal, analyzes an acoustic characteristic of a specific type of sound in the speech signal and outputs the acoustic characteristic;
   a conversion unit that accepts input of the acoustic characteristic being output from the analysis unit, generates and outputs a vibration signal of a duration corresponding to the acoustic characteristic and outputs the vibration signal; and
   a presentation unit that accepts input of the vibration signal being output from the conversion unit and provides the user with vibration for the duration on the basis of the vibration signal.

Effects of the Invention

The technology disclosed herein provides a technology enabling realization of speech hearing assistance through leveraging tactual information in speech hearing, requiring neither training of a user nor an elaborate apparatus.

DESCRIPTION OF EMBODIMENTS

Hereinafter, an embodiment of the present invention (present embodiment) is described with reference to the drawings. The embodiment described below is merely an example, and an embodiment to which the present invention is applied is not limited to the embodiment below.

Regarding Experiment

The technology according to the present embodiment leverages a phenomenon that a vibration stimulus relating to articulatory movement and acoustic input of speech are integrated on the user side.

In other words, on the basis of an illusion phenomenon caused by a relationship between speech production and hearing, hearing assistance is carried out by presenting to a user a stimulus that can transmit speech as a tactual sense. First, details and results of an experiment serving as a basis for the above-described phenomenon will be described.

In this experiment, ten subjects heard speech "ba" and "pa" masked with noise, while receiving vibrations of various durations on the back of the hand.

Figure 1:
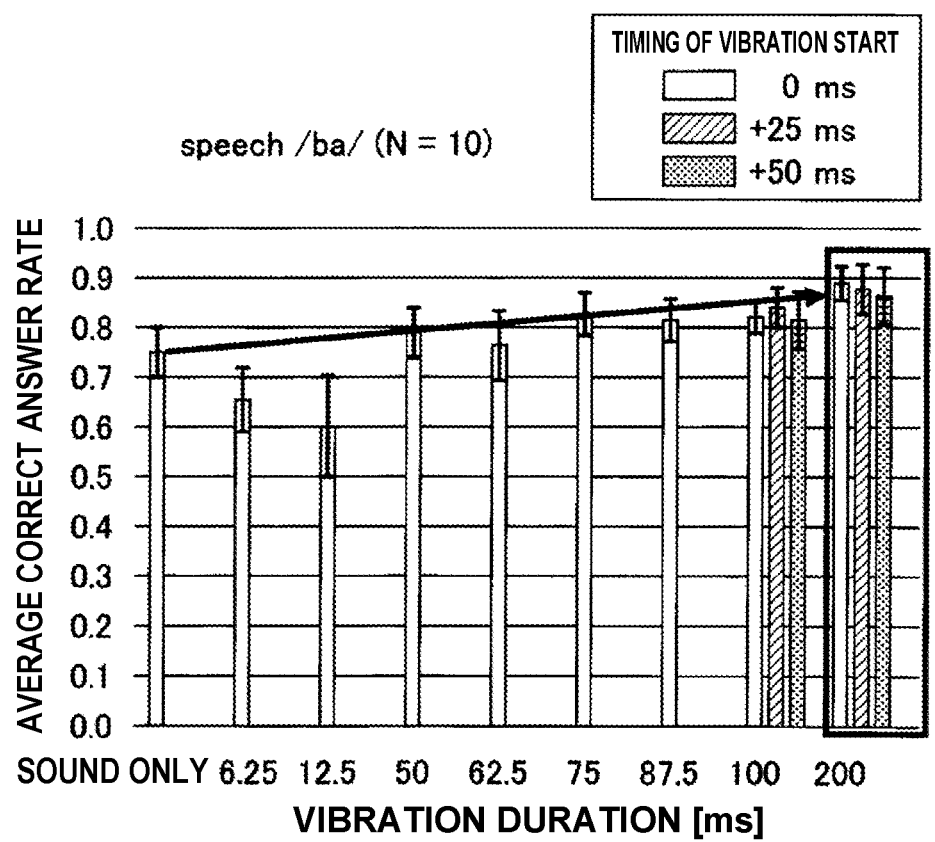
FIG. 1 is a diagram showing an experimental result.
Figure 2:
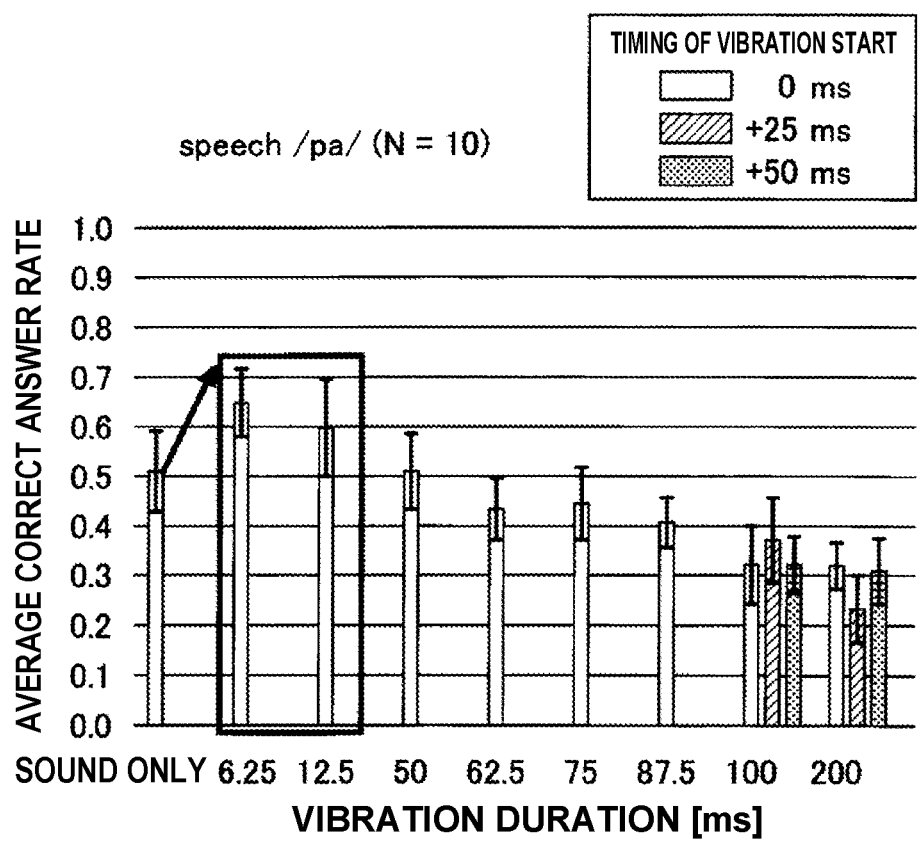
FIG. 2 is a diagram showing an experimental result.

FIG. 1 shows an experimental result regarding "ba". As shown in FIG. 1, it has been found that the speech is likely to be heard as "ba" with the vibration of a duration of 200 ms. FIG. 2 shows an experimental result regarding "pa". As shown in FIG. 2, it has been found that the speech is likely to be heard as "pa" with the vibration of a duration of 6.25 to 12.5 ms.

In addition, it has been found from the experiment that a similar effect can be obtained with a delay of about 50 ms in the timing of start of the vibration being allowed.

Hereinafter, a person who hears speech and receives presentation of vibration will be referred to as a "user". When speech information is input to an auditory sense of the user, even if the speech information is compromised on the user side due to noise or hearing disorder, the present embodiment enables the user to clearly hear the speech in conversion and the like through inputting vibration from a tactual sense of the user to cause integration with the remaining auditory information.

In the present embodiment, the speech transmission compensation apparatus presents the vibration to the user. Note that "present the vibration to the user" may be stated otherwise as "provide the user with the vibration", "input the vibration to the user" and the like.

Hereinafter, the configuration and the operation of the speech transmission compensation apparatus according to the present embodiment are described in detail with reference to Example 1, Example 2 and Variation.

Example 1

First, Example 1 will be described. In Example 1, while the user hears real-time speech in the conversation and the like, a speech transmission compensation apparatus 100 facilitates the user to discriminate the speech such as "ba/pa" even in a noisy environment or with hearing disorder, through presenting the vibration to the user. Note that in Example 1 (and Example 2), a description will be given for discrimination between voiced plosives /b/, /d/, /g/ and unvoiced plosives /p/, /t/, /k/, as an example.

Apparatus Configuration Example

Figure 3:
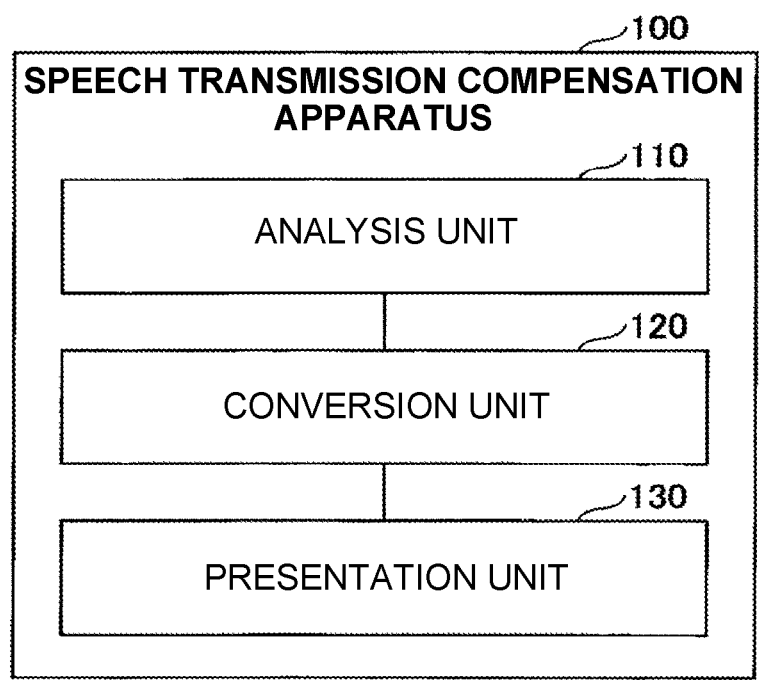
FIG. 3 is a configuration diagram of a speech transmission compensation apparatus of Example 1.

FIG. 3 shows a configuration diagram of the speech transmission compensation apparatus 100 of Example 1. As shown in FIG. 3, the speech transmission compensation apparatus 100 of Example 1 is provided with an analysis unit 110, a conversion unit 120 and a presentation unit 130.

The speech transmission compensation apparatus 100 may be, for example, either a smartphone or the like provided with a vibration element (vibrator), or other apparatuses.

Input and output of the units are described hereafter, while details of processing of the units will be described in an operation description provided later with reference to a flow chart.

The analysis unit 110 accepts a speech signal as an input, and outputs information indicating whether a duration from a starting time of a plosive waveform, which is included in the speech signal being input, to a starting time of a periodic waveform is greater than or equal to a predetermined duration (for example 25 ms in this example, the same applies hereinafter).

Note that the plosive waveform refers to a speech waveform part of a plosion caused by an articulatory apparatus of a speaker being suddenly released after occlusion. In addition, a plosive refers to all consonants (/b/, /p/, /d/, /t/ and the like) including a plosive feature (part with the plosive waveform) along with other phonetic features.

The conversion unit 120 accepts the information indicating whether the duration is greater than or equal to 25 ms as an input, and outputs a vibration signal. The presentation unit 130 accepts the vibration signal as an input and outputs vibration.

Operation Example of Speech Transmission Compensation Apparatus 100

Next, an operation example of the speech transmission compensation apparatus 100 of Example 1 is described. First, an outline is described. In the speech transmission compensation apparatus 100, first, a speech signal heard by the user is input to the analysis unit 110. Then, the analysis unit 110 analyzes an acoustic characteristic of a specific type of sound in the speech signal, and outputs the acoustic characteristic.

Next, the conversion unit 120 accepts input of the acoustic characteristic being output from the analysis unit 110, and generates and outputs a vibration signal of a duration corresponding to the acoustic characteristic. Subsequently, the presentation unit 130 accepts input of the vibration signal being output from the conversion unit 120 and provides the user with vibration for the duration on the basis of the vibration signal.

In Example 1, the specific type of sound is a plosive. The analysis unit 110 outputs, as the acoustic characteristic, information indicating whether a duration from a starting time of a plosive waveform in the plosive to a starting time of a periodic waveform is greater than or equal to a predetermined threshold.

Hereinafter, an operation example of the speech transmission compensation apparatus 100 of Example 1 is described in detail according to the procedure of the flow chart in FIG. 4. FIG. 5 showing a speech waveform is also referenced accordingly.

As shown in FIG. 5, which is a waveform of a speech signal of a plosive such as "ba"/"pa", the plosive included in the speech signal has a characteristic of starting with a plosive waveform, followed by a periodic waveform after a certain period of time. The processing by the analysis unit 110 is based on such a characteristic.

Figure 4:
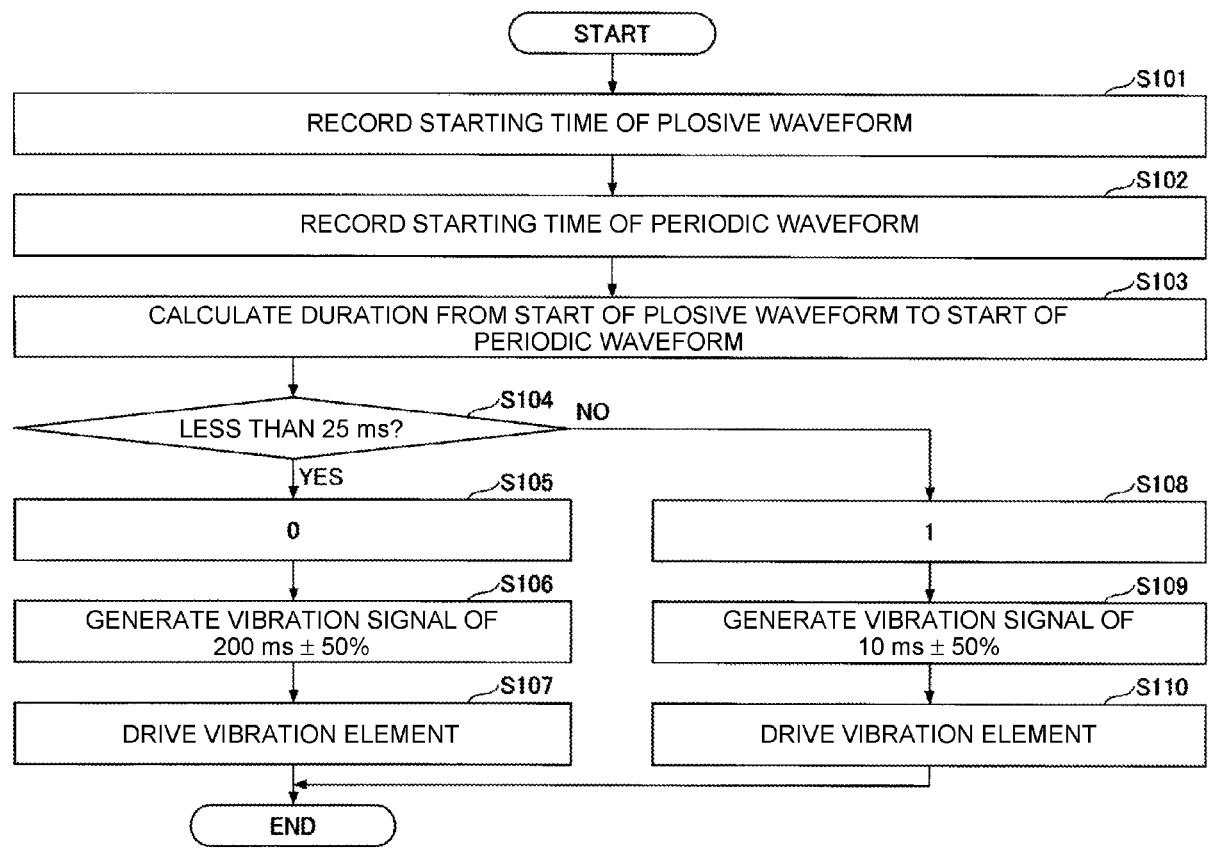
FIG. 4 is a flow chart for explaining an operation of the speech transmission compensation apparatus of Example 1.
Figure 5:
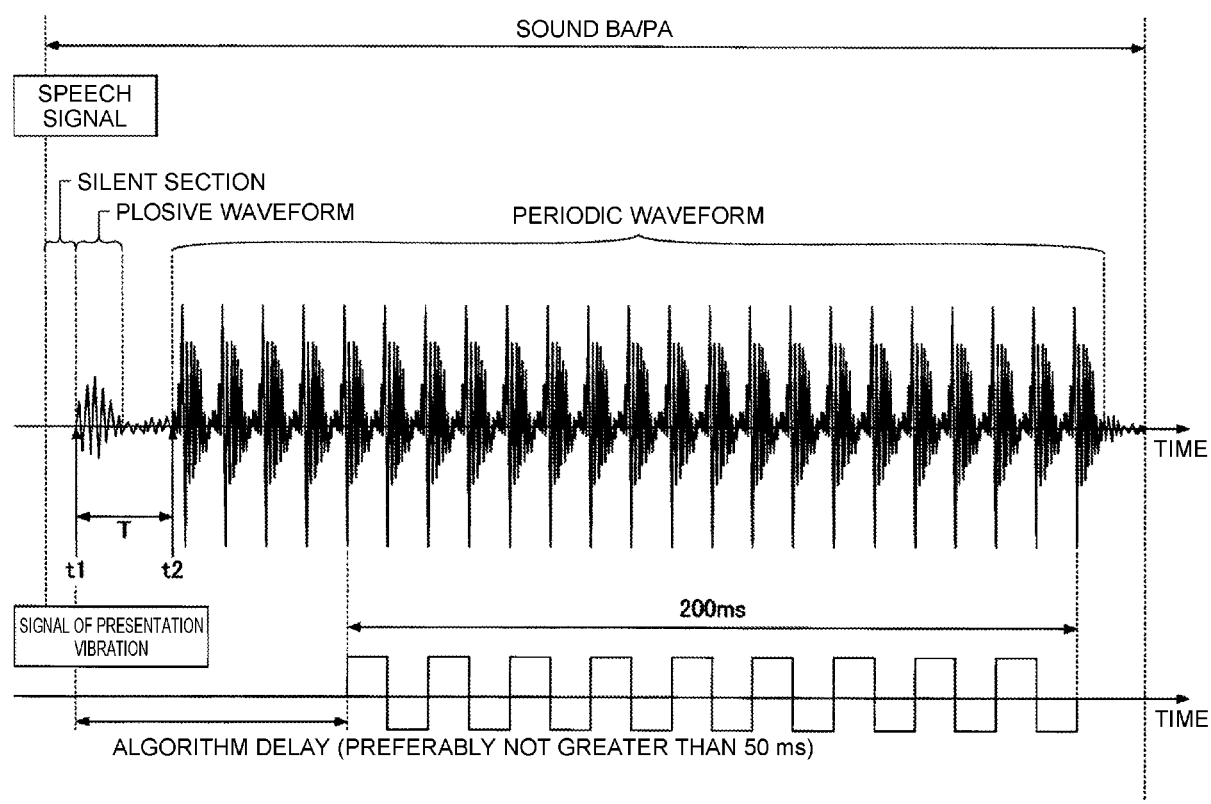
FIG. 5 is a diagram for explaining details of processing.

In S101 in FIG. 4, the analysis unit 110 having accepted input of the speech signal detects a plosive waveform in the waveform of the speech signal and records a starting time t1 of the plosive waveform.

A method for obtaining the starting time is not limited to a specific method and may be, for example, a method of detecting a local peak of a spectrum typically used for detection of a plosive consonant, or a method of detecting a burst waveform from 5 ms to 40 ms appearing after a silent section from 50 ms to 100 ms.

In S102, the analysis unit 110 detects a periodic waveform immediately after the plosive waveform and records a starting time t2 of the periodic waveform.

In S103, the analysis unit 110 calculates a duration from the start of the plosive waveform to the start of the periodic waveform, t2 − t1 = T. T is referred to as Voice Onset Time. Specific examples of t1, t2 and T in S101 to S103 are as shown in FIG. 5.

In S104, the analysis unit 110 compares T with the predetermined threshold in regard to a magnitude relationship. It is supposed that a value enabling identification of two speech sounds to be discriminated is obtained in advance by an experiment and the like, and is set to the analysis unit 110 as the predetermined threshold. In this example, the predetermined threshold is 25 ms, supposing discrimination between "b" and "p", for example.

The analysis unit 110 outputs: 0 in S105 when T is determined to be smaller than the predetermined threshold (25 ms); and 1 in S108 when T is determined to be greater than or equal to the predetermined threshold (25 ms). The value 0 or 1 being output from the analysis unit 110 is input to the conversion unit 120.

The periodic waveform starting after a predetermined period of time from the plosive waveform indicates vocal fold vibration. A characteristic has been known that the duration from the plosion to the start of vocal fold vibration is short in a voiced plosive, and long in an unvoiced plosive. Therefore, when the output from the analysis unit 110 is 0, the speech signal (plosive) being input can be determined to correspond to "b", while when the output from the analysis unit 110 is 1, the speech signal (plosive) being input can be determined to correspond to "p". Note that setting 25 ms as the predetermined threshold is an example, and a value other than 25 ms may also be set in consideration of a difference between individuals and the like. In addition, the information indicating whether T is smaller than the predetermined threshold is not limited to the value 0 or 1.

When 0 is input from the analysis unit 110 to the conversion unit 120, in S106, the conversion unit 120 generates and outputs a vibration signal for presenting a vibration stimulus of a duration of about one syllable (e.g., 200 ms ± 50%). The vibration signal thus output is input to the conversion unit 130.

When 1 is input from the analysis unit 110 to the conversion unit 120, in S109, the conversion unit 120 generates and outputs a vibration signal for presenting a vibration stimulus of a duration of about the shortest cycle permitting the user (person) to feel the vibration (e.g., 10 ms ± 50%). The vibration signal thus output is input to the conversion unit 130.

The duration of presentation of vibration by the vibration signal and a type of the vibration signal may also be defined according to a type of an apparatus in which the presentation unit 130 is implemented (e.g., a vibration element in a smartphone). In addition, 200 ms and 10 ms are examples based on the aforementioned experiment, and other values suited to an individual may be set in consideration of a difference between individuals and the like.

The presentation unit 130 includes a vibration element (which may also be referred to as a vibrator). In each of S107 and S110, the presentation unit 130 having accepted input of the vibration signal drives the vibration element on the basis of the vibration signal to present vibration to the user.

The presentation unit 130 is a functional unit that is composed of, for example, a vibration element and a function of driving the vibration element included in a smartphone or the like, and presents vibration by vibrating the vibration element. A body part of the user to which the vibration is presented is for example, but not limited to, a hand and the like. The effect of this phenomenon is maintained, and thus integration of the real-time speech and the vibration on the user side is ensured, when a delay between the plosive feature in the speech and presentation of the vibration is no greater than 50 ms. Note that "50 ms" is an example of the acceptable delay. FIG. 5 shows an example of presenting the vibration of 200 ms.

The above-described technology according to Example 1 can assist speech hearing in such a way that discrimination between hardly distinguished speech is enabled even in a noisy environment or with hearing disorder, through leveraging tactual information (vibration) in speech hearing, requiring neither training of a user nor an elaborate apparatus.

Example 2

Example 1 has been described exemplifying the case in which the user hears real-time speech in conversation and the like; however, application of the technology according to the present invention is not limited thereto. For example, the technology according to the present invention may also be applied to hearing of recorded speech such as news.

An example of applying the present invention to hearing of recorded speech such as news is described as Example 2. In Example 2, by storing the time at which the plosive waveform is generated in the speech signal and an acoustic characteristic corresponding to the plosive waveform (0 or 1 described in Example 1) in association with each other, the speech being played back and the vibration are integrated to present the vibration to the user with no delay, whereby assistance of speech hearing is enabled.

Apparatus Configuration Example

Figure 6:
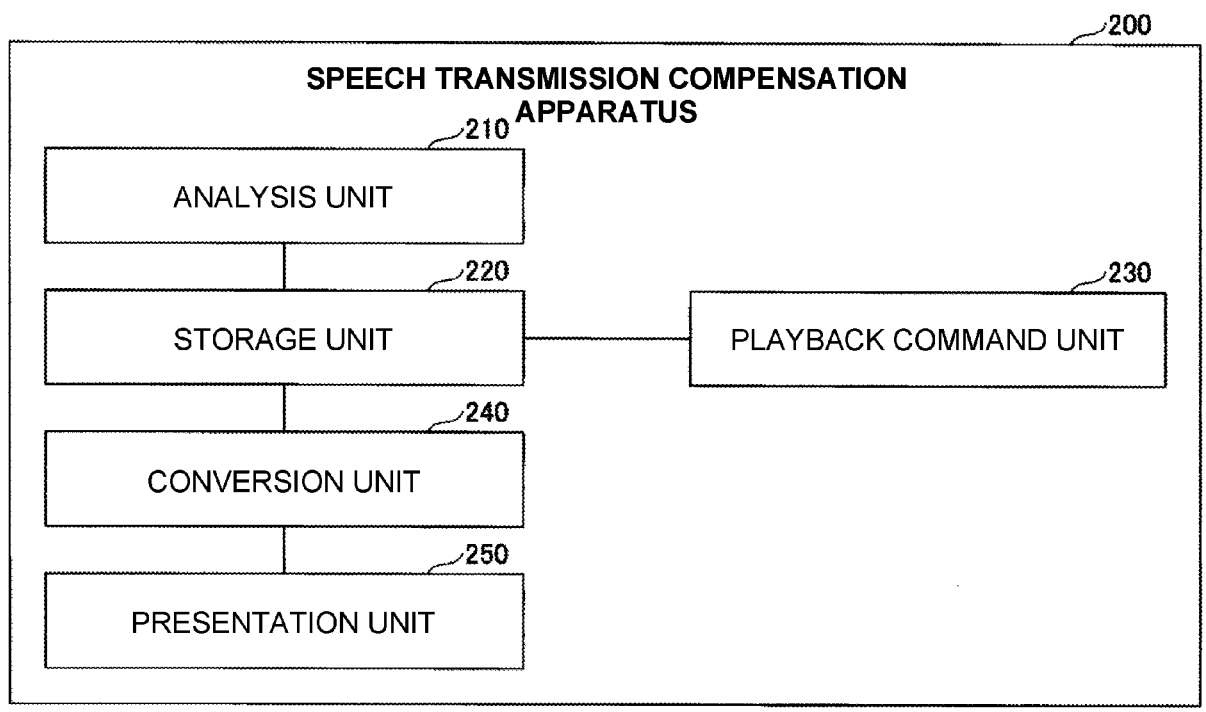
FIG. 6 is a configuration diagram of a speech transmission compensation apparatus of Example 2.

FIG. 6 shows a configuration diagram of the speech transmission compensation apparatus 200 of Example 2. As shown in FIG. 6, the speech transmission compensation apparatus 200 of Example 2 is provided with an analysis unit 210, a storage unit 220, a playback command unit 230, a conversion unit 240 and a presentation unit 250.

As in Example 1, the speech transmission compensation apparatus 200 may be, for example, either a smartphone or the like provided with a vibration element (vibrator), or other terminals.

Input and output of the units are described hereafter, and details of processing of the units are described in an operation description provided later, with reference to a flow chart.

The analysis unit 210 accepts a speech signal as an input, and outputs: information of time $t1\_k$ at which the plosive feature is present regarding each k (k = 1 to N), and information indicating whether a duration Tk from the start thereof (start time of the plosive waveform k) to the start of a periodic waveform is greater than or equal to a predetermined duration (for example 25 ms in this example, the same applies hereinafter). Although in the present example the starting time of the plosive waveform k is defined as the time $t1\_k$ at which the plosive feature is present; however, the time at which the plosive feature is present may also be other than the starting time.

The number k represents the cumulative number of occurrences of the plosive waveforms included in the speech signal in time series (k = 0, 1, 2, ... N; N being the total number of plosive waveforms). Note that when N = 0, the plosive waveform is not present. In the present embodiment, N ≥ 1, since the plosive waveform is supposed to be present.

The storage unit 220 accepts, as an input, the information of time $t1\_k$ at which the plosive feature is present regarding each k (k = 1 to N), and the information indicating whether the duration Tk from the start thereof (start time of the plosive waveform k) to the start of a periodic waveform is greater than or equal to 25 ms. In addition, the storage unit 220 also accepts a playback command as an input. The storage unit 220 outputs, on the basis of the playback command, the information of time $t1\_k$ at which the plosive feature is present regarding each k (k = 1 to N), and the information indicating whether the duration Tk from the start thereof (start time of the plosive waveform k) to the start of a periodic waveform is greater than or equal to 25 ms.

The conversion unit 240 accepts, as an input, the information of time t1_k at which the plosive feature is present regarding each k (k = 1 to N), and the information indicating whether the duration Tk from the start thereof (start time of the plosive waveform k) to the start of a periodic waveform is greater than or equal to 25 ms, and outputs a vibration signal at each time t1_k.

The presentation unit 250 accepts the vibration signal as an input and outputs vibration. The playback command unit 230 accepts playback start information of the speech signal as an input, and outputs the playback command.

Operation Example of Speech Transmission Compensation Apparatus 200

Figure 7:
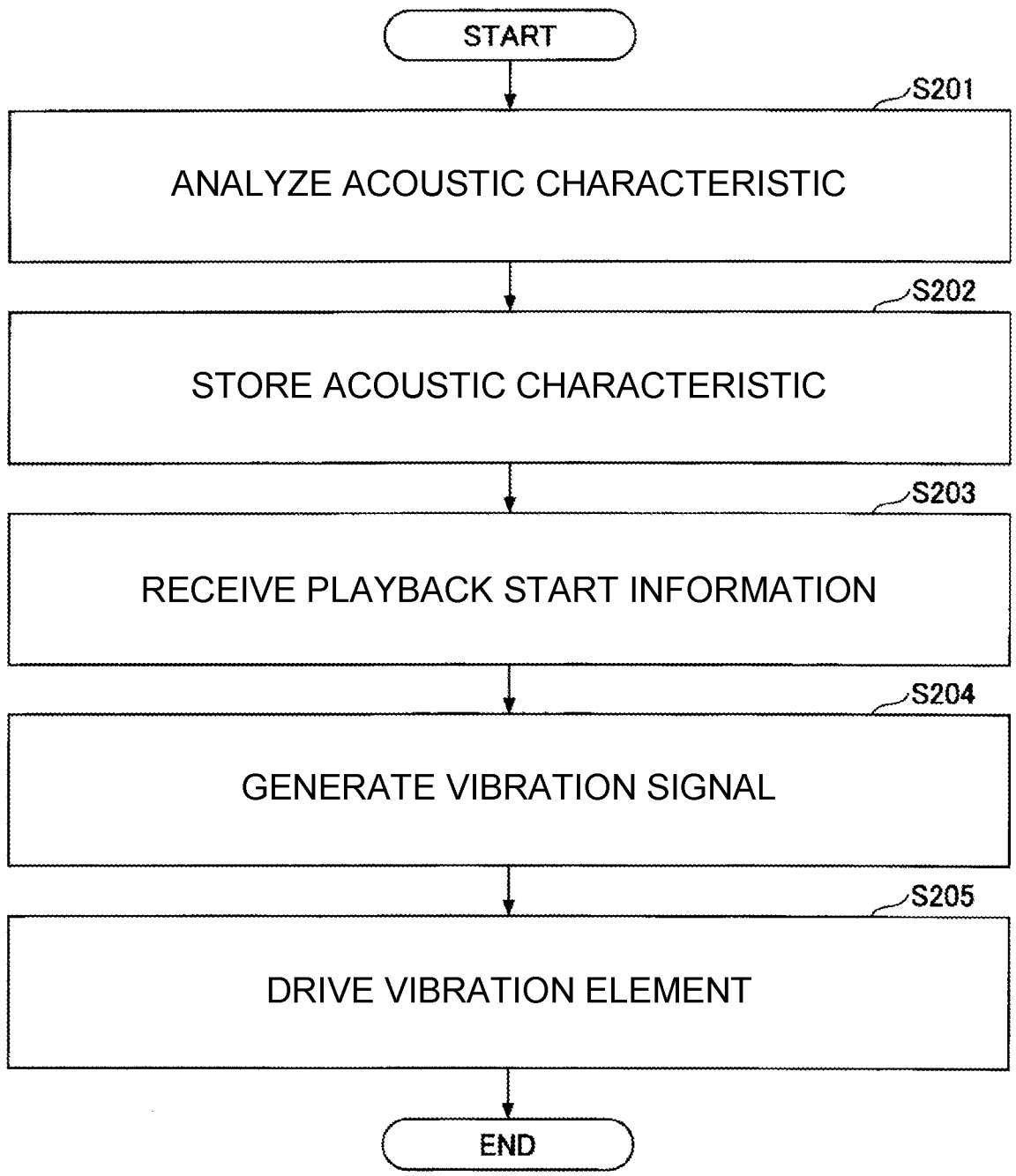
FIG. 7 is a flow chart for explaining an operation of the speech transmission compensation apparatus of Example 2.

Next, an operation example of the speech transmission compensation apparatus 200 of Example 2 is described according to the procedure of the flow chart in FIG. 7. Since basic processing details for presenting vibration in Example 2 are the same as Example 1, the flow chart in FIG. 4 and FIG. 5 are referenced accordingly. Note that "time" in Example 2 is relative time, with the start of the recorded speech being 0.

In S201, the analysis unit 210 having accepted input of the speech signal of the recorded speech analyzes an acoustic characteristic of the speech signal. As described in Example 1, the plosive included in the speech has a characteristic of starting with a plosive waveform, followed by a periodic waveform after a certain period of time. The processing by the analysis unit 210 is based on such a characteristic. As in Example 1, the acoustic characteristic in Example 2 is information indicating whether a duration from a starting time of a plosive waveform in the plosive to a starting time of a periodic waveform is greater than or equal to a predetermined threshold.

More specifically, in S201, the processing similar to S101 to S103, S104, S105 and S108 in FIG. 4 is carried out for each plosive waveform. However, in Example 2, the information thus obtained is stored in the storage unit 220 (S202 in FIG. 7). Specific description thereof is given below. Hereinafter, the step numerals shown in FIG. 4 will be used for the sake of convenience.

The analysis unit 210 calculates the duration Tk for all plosive waveforms and an immediate subsequent periodic waveform included in a target speech signal. And then, the analysis unit 210 carries out, for each k, S101 to S103, S104, S105 and S108 described below. In other words, the following processing is carried out for each of k = 1, 2, ... N.

In S101, the analysis unit 210 detects a plosive waveform in the waveform of the speech signal and records and outputs a starting time t1_k of the plosive waveform. The starting time t1_k thus output is stored in the storage unit 220. The method for obtaining the starting time is as described in Example 1.

In S102, the analysis unit 210 detects a periodic waveform immediately after the plosive waveform and records a starting time t2_k of the periodic waveform.

In S103, the analysis unit 210 calculates a duration from the start of the plosive waveform to the start of the periodic waveform, t2_k-t1_k=Tk.

In S104, the analysis unit 210 compares Tk with the predetermined threshold in regard to a magnitude relationship. It is supposed that a value enabling identification of two speech sounds to be discriminated is obtained in advance by an experiment and the like, and is set to the analysis unit 210 as a predetermined threshold. In this example, as in Example 1, the predetermined threshold is 25 ms, supposing discrimination between "b" and "p" for example.

The analysis unit 210 outputs: 0 in S105 when Tk is determined to be smaller than the predetermined threshold (25 ms), and 1 in S108 when Tk is determined to be greater than or equal to the predetermined threshold (25 ms). The value 0 or 1 being output from the analysis unit 210 is stored in the storage unit 220. As a result, for each plosive waveform k, the storage unit 220 stores the starting time t1_k thereof, and 0 or 1 in association with each other.

As described in Example 1, the periodic waveform indicates vocal fold vibration, and a characteristic is known that the duration from the plosion to the start of vocal fold vibration is short in a voiced plosive, and long in an unvoiced plosive. Therefore, when the output from the analysis unit 210 is 0, the speech signal (plosive) can be determined to correspond to "b", while when the output from the analysis unit 210 is 1, the speech signal (plosive) can be determined to correspond to "p". Note that setting 25 ms as the predetermined threshold is an example, and it is preferred to set the threshold in consideration of a difference between individuals and the like.

In S203 in FIG. 7, the playback command unit 230 receives playback start information. The playback start information is, for example, information indicating that playback of an original speech signal, which is an original of the information stored in the storage unit 220 by the aforementioned processing, has been started.

The playback command unit 230 having received the playback start information outputs the playback command to the storage unit 220. The storage unit 220 having received the playback command outputs the information of time t1_k at which the plosive feature is present regarding each k (k = 1 to N), and the information indicating whether the duration Tk from the plosive feature to the start of a periodic waveform is greater than or equal to 25 ms. These pieces of information thus output are input to the conversion unit 240. Note that, it may also be configured that the conversion unit 240 receives the playback command, and according to the playback command, reads from the storage unit 220 the information of time t1_k at which the plosive feature is present regarding each k (k = 1 to N), and the information indicating whether the duration Tk from the plosive feature to the start of a periodic waveform is greater than or equal to 25 ms.

In S204 in FIG. 7, the conversion unit 240 generates and outputs, for each k (k = 1 to N), a vibration signal at the time t1_k in a similar manner to S106 and S109 in Example 1. The vibration signal is input to the presentation unit 250. Specific description thereof is given below.

When it is detected that "the information indicating whether the duration Tk from the plosive feature to the start of a periodic waveform is greater than or equal to 25 ms" is 0 at the time t1_k from the start of playback, the conversion unit 240 generates and outputs a vibration signal for presenting a vibration stimulus of a duration of about one syllable (e.g., 200 ms ± 50%). The vibration signal thus output is input to the presentation unit 250.

When it is detected that "the information indicating whether the duration Tk from the plosive feature to the start of a periodic waveform is greater than or equal to 25 ms" is 1 at the time t1_k from the start of playback, the conversion unit 240 generates and outputs a vibration signal for presenting a vibration stimulus of a predetermined duration defined in advance. Here, for example, the conversion unit 240 generates a vibration signal for presenting a vibration stimulus of a duration of about the shortest cycle permitting the user (person) to feel the vibration (e.g., 10 ms ± 50%). The vibration signal thus output is input to the presentation unit 250.

The duration of presentation of vibration by the vibration signal and a type of the vibration signal may also be defined according to a type of an apparatus in which the presentation unit 250 is implemented (e.g., a vibration element of a smartphone). In addition, 200 ms and 10 ms are examples based on the aforementioned experiment, and values other than 200 ms and 10 ms suited to an individual may be set in consideration of a difference between individuals and the like.

The presentation unit 250 is a functional unit that is composed of, for example, a vibration element and a function of driving the vibration element included in a smartphone or the like, and in S205, presents vibration by vibrating the vibration element. A body part of the user to which the vibration is presented is for example, but not limited to, a hand and the like. The effect of this phenomenon is maintained, and thus integration of the real-time speech and the vibration on the user side is ensured when a delay between the plosive feature in the speech and presentation of the vibration is no greater than 50 ms. Note that "50 ms" is an example.

The above-described technology according to Example 2 can also assist speech hearing in such a way that discrimination between hardly distinguished speech is enabled even in a noisy environment or with hearing disorder, through leveraging tactual information (vibration) in speech hearing, requiring neither training of a user nor an elaborate apparatus.

Variation

Note that in Example 1 and Example 2, descriptions have been given for discrimination between voiced plosives /b/, /d/, /g/ and unvoiced plosives /p/, /t/, /k/ as an example with a focus on the human vocal fold vibration during speech; however, the present invention is not limited thereto. For example, the technology according to the present invention may also be applied to nasals /n/, /m/, fricatives /s/, /z/ and the like, to assist discrimination of nasals /n/, /m/, discrimination of fricatives /s/, /z/ and the like. In other words, with nasals /n/, /m/, fricatives /s/, /z/, and the like, by providing the user with vibration imitating a cutaneous sensation generated during speech production as in Examples 1 and 2, assistance of discrimination of speech is enabled.

A vibration duration imitating the cutaneous sensation may be accordingly defined in advance by an experiment and the like.

Hardware Configuration Example

The speech transmission compensation apparatuses according to the present embodiment may be realized by, for example, causing a computer to execute a program in which the processing described in the present embodiment is recorded. Note that the "computer" includes a smartphone and the like.

The aforementioned program may be stored and distributed in a state of being recorded in a computer-readable recording medium (such as portable memory). The aforementioned program may also be provided via a network, by way of the Internet, e-mailing and the like.

Figure 8:
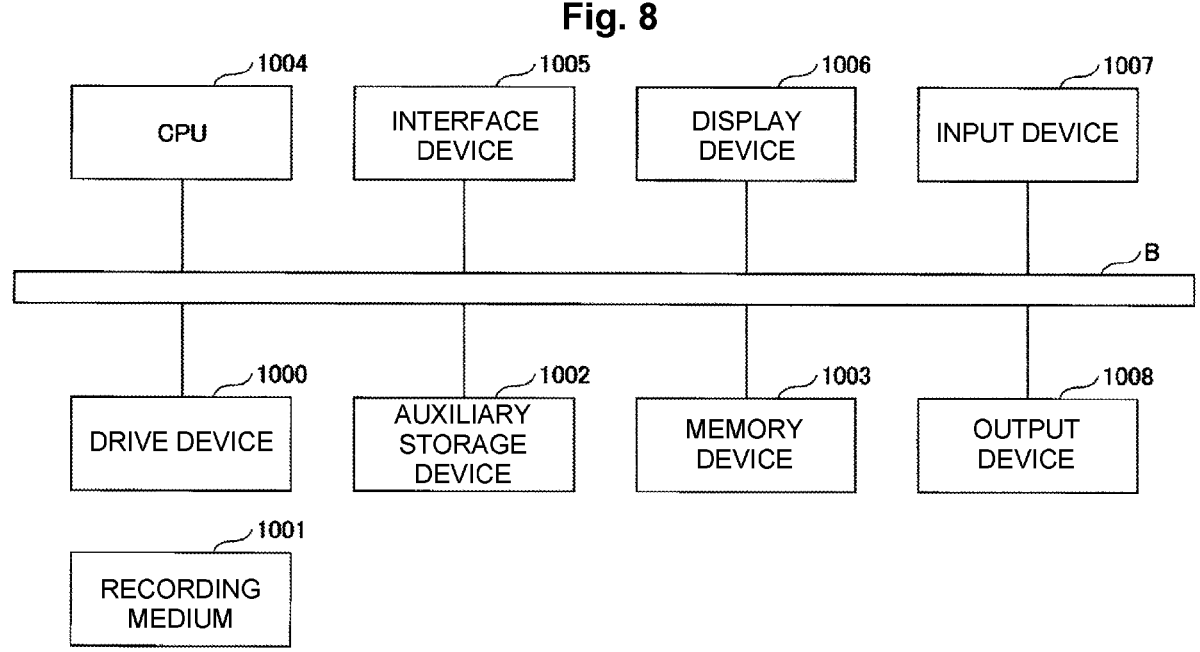
FIG. 8 is a diagram showing a hardware configuration example of the apparatus.

FIG. 8 is a diagram showing a hardware configuration example of the computer. The computer in FIG. 8 includes: a drive device 1000, an auxiliary storage device 1002, a memory device 1003, a CPU 1004, an interface device 1005, a display device 1006, an input device 1007, an output device 1008 and the like, connected to each other via a bus B.

The program for realizing the processing in the computer is provided in, for example, a recording medium 1001 such as a CD-ROM or a memory card. When the recording medium 1001 in which the program is stored is set to the drive device 1000, the program is installed from the recording medium 1001 to the auxiliary storage device 1002 via the drive device 1000. However, the installation of the program is not necessarily required to be done from the recording medium 1001, and the program may be configured to be downloaded from another computer via a network. The auxiliary storage device 1002 stores the program thus installed, as well as necessary files and data.

When a running instruction of the program is given, the memory device 1003 reads and stores the program from the auxiliary storage device 1002. The CPU 1004 realizes a function related to the apparatus, in accordance with the program stored in the memory device 1003. The interface device 1005 is used as an interface for connecting to a network. The display device 1006 displays a graphical user interface (GUI) and the like by the program.

The input device 1007 in the present embodiment is, for example, a microphone for inputting the speech signal. In addition, the input device 1007 may include a touch screen for inputting various operation instructions. The output device 1008 in the present embodiment outputs vibration.

Summary of Embodiment

The present specification discloses at least a speech transmission compensation apparatus, a speech transmission compensation method and a program described in the following sections.

Section 1

A speech transmission compensation apparatus that assists discrimination of speech heard by a user, including:
- an analysis unit that accepts input of a speech signal, analyzes an acoustic characteristic of a specific type of sound in the speech signal and outputs the acoustic characteristic;
- a conversion unit that accepts input of the acoustic characteristic being output from the analysis unit, generates and outputs a vibration signal of a duration corresponding to the acoustic characteristic and outputs the vibration signal; and
- a presentation unit that accepts input of the vibration signal being output from the conversion unit and provides the user with vibration for the duration on the basis of the vibration signal.

Section 2

The speech transmission compensation apparatus according to Section 1, wherein: the specific type of sound is a plosive; and the analysis unit outputs, as the acoustic characteristic, information indicating whether a duration from a starting time of a plosive waveform in the plosive to a starting time of a periodic waveform is greater than or equal to a predetermined threshold.

Section 3

The speech transmission compensation apparatus according to Section 1 or 2, further comprising a storage unit, wherein:
the analysis unit stores into the storage unit, at every time point where the specific type of sound is detected, the time point and the acoustic characteristic obtained from the speech signal at the time point; and
the conversion unit, at each time point being read from the storage unit, generates a vibration signal corresponding to the acoustic characteristic at the time point and outputs the vibration signal.

Section 4

A speech transmission compensation method carried out by a speech transmission compensation apparatus that assists discrimination of speech heard by a user, comprising:
an analysis step of analyzing an acoustic characteristic of a specific type of sound in a speech signal being input;
a conversion step of generating a vibration signal of a duration corresponding to the acoustic characteristic obtained in the analysis step; and
a presentation step of providing the user with vibration for the duration on the basis of the vibration signal obtained in the conversion step.

Section 5

A program that causes a computer to function as the units in the speech transmission compensation apparatus according to any one of Sections 1 to 3.

The present embodiment has been described in the foregoing; however, the present invention is not limited to the specific embodiment and various modifications and alterations can be made without departing from a scope of the spirit of the present invention described in the Claims.

| Reference Signs List | |
|---|---|
| 100, 200 | Speech transmission compensationapparatus |
| 110, 210 | Analysis unit |
| 120, 240 | Conversion unit |
| 130, 250 | Presentation unit |
| 220 | Storage unit |
| 230 | Playback command unit |
| 1000 | Drive device |
| 1001 | Recording medium |
| 1002 | Auxiliary storage device |
| 1003 | Memory device |
| 1004 | CPU |
| 1005 | Interface device |
| 1006 | Display device |
| 1007 | Input device |
| 1008 | Output device |

The invention claimed is:

1. A speech transmission compensation apparatus that assists discrimination of speech heard by a user, comprising:
one or more computers each including a memory and a processor configured to:
accept input of a speech signal, detect a specific type of sound in the speech signal, wherein the specific type of sound is a plosive;
analyze an acoustic characteristic of the specific type of sound in the speech signal and output the acoustic characteristic;
accept input of the acoustic characteristic being output by the memory and the processor, generate a vibration signal of a duration corresponding to the acoustic characteristic and output the vibration signal; and
accept input of the vibration signal being output by the memory and the processor and provide the user with vibration for the duration on the basis of the vibration signal, wherein the acoustic characteristic comprises information indicating whether a duration from a starting time of a plosive waveform to a starting time of a periodic waveform in the plosive is greater than or equal to a predetermined threshold.

2. The speech transmission compensation apparatus according to claim 1, further comprising a a storage, wherein:
the processor is further configured to store into the storage, at every time point where the specific type of sound is detected, the time point and the acoustic characteristic obtained from the speech signal at the time point; and
the memory and the processor are further configured to, at each time point being read from the storage, generate a vibration signal corresponding to the acoustic characteristic at the time point and output the vibration signal.

3. A speech transmission compensation method carried out by a speech transmission compensation apparatus that assists discrimination of speech heard by a user, comprising:
analyzing an acoustic characteristic of a specific type of sound in a speech signal being input, wherein the specific type of sound is a plosive;
generating a vibration signal of a duration corresponding to the acoustic characteristic obtained by the analysing; and
providing, by the speech transmission compensation apparatus, the user with vibration for the duration on the basis of the vibration signal obtained by the generating, wherein the acoustic characteristic comprises information indicating whether a duration from a starting time of a plosive waveform to a starting time of a periodic waveform in the plosive is greater than or equal to a predetermined threshold.

4. A non-transitory compuer-readable recording medium having computer-readable instructions stored thereon, which when executed cause a computer including a memory and a proessor to execute respective operations in the speech transmission compensation apparatus according to claim 1.

* * * * *